(12) United States Patent
Vaezy et al.

(10) Patent No.: US 7,670,291 B2
(45) Date of Patent: Mar. 2, 2010

(54) INTERFERENCE-FREE ULTRASOUND IMAGING DURING HIFU THERAPY, USING SOFTWARE TOOLS

(75) Inventors: Shahram Vaezy, Seattle, WA (US);
Robert Held, Issaquah, WA (US);
Siddhartha Sikdar, Seattle, WA (US);
Ravi Managuli, Seattle, WA (US);
Vesna Zderic, Seattle, WA (US)

(73) Assignee: University of Washington, Seattle, WA (US)

( * ) Notice: Subject to any disclaimer, the term of this patent is extended or adjusted under 35 U.S.C. 154(b) by 1202 days.

(21) Appl. No.: 11/229,000

(22) Filed: Sep. 16, 2005

(65) Prior Publication Data

US 2006/0264748 A1    Nov. 23, 2006

Related U.S. Application Data

(60) Provisional application No. 60/610,456, filed on Sep. 16, 2004.

(51) Int. Cl.
*A61B 8/00*    (2006.01)

(52) U.S. Cl. .................. 600/439; 600/437; 600/440; 600/441; 600/443; 600/459; 601/1; 601/2

(58) Field of Classification Search .............. 601/1, 601/2; 600/437, 459, 439, 440, 441, 443
See application file for complete search history.

(56) References Cited

U.S. PATENT DOCUMENTS

RE33,590 E    5/1991  Dory ................... 128/660.03
5,039,774 A   8/1991  Shikinami et al. ........... 528/60
5,065,742 A   11/1991 Belikan et al. ............... 128/24
5,080,101 A   1/1992  Dory .................... 128/660.03

(Continued)

FOREIGN PATENT DOCUMENTS

DE    04230415 A1    3/1994

(Continued)

OTHER PUBLICATIONS

"Mechanical Bioeffects in the prescence of gas/carrier ultrasound contrast agents." J Ultrasound Med. 19: 120/142, 2000.

(Continued)

*Primary Examiner*—Brian Casler
*Assistant Examiner*—John F Ramirez
(74) *Attorney, Agent, or Firm*—Ronald M. Anderson

(57) ABSTRACT

Disclosed herein is a method for obtaining a composite interference-free ultrasound image when non-imaging ultrasound waves would otherwise interfere with ultrasound imaging. A conventional ultrasound imaging system is used to collect frames of ultrasound image data in the presence of non-imaging ultrasound waves, such as high-intensity focused ultrasound (HIFU). The frames are directed to a processor that analyzes the frames to identify portions of the frame that are interference-free. Interference-free portions of a plurality of different ultrasound image frames are combined to generate a single composite interference-free ultrasound image that is displayed to a user. In this approach, a frequency of the non-imaging ultrasound waves is offset relative to a frequency of the ultrasound imaging waves, such that the interference introduced by the non-imaging ultrasound waves appears in a different portion of the frames.

20 Claims, 9 Drawing Sheets

U.S. PATENT DOCUMENTS

| | | | |
|---|---|---|---|
| 5,080,102 A | 1/1992 | Dory | 128/660.03 |
| 5,150,712 A | 9/1992 | Dory | 128/660.03 |
| 5,219,401 A | 6/1993 | Cathignol et al. | 128/660.03 |
| 5,311,869 A | 5/1994 | Okazaki | 128/660.03 |
| 5,391,140 A | 2/1995 | Schaetzle et al. | 601/4 |
| 5,394,877 A | 3/1995 | Orr et al. | 600/459 |
| 5,471,988 A | 12/1995 | Fujio et al. | 128/660.03 |
| 5,474,071 A | 12/1995 | Chapelon et al. | 600/439 |
| 5,492,126 A | 2/1996 | Hennige et al. | 600/439 |
| 5,507,790 A | 4/1996 | Weiss | 607/100 |
| 5,522,878 A | 6/1996 | Montecalvo et al. | 607/152 |
| 5,526,815 A | 6/1996 | Granz et al. | 128/660.03 |
| 5,558,092 A | 9/1996 | Unger et al. | 128/600.03 |
| 5,573,497 A | 11/1996 | Chapelon | 601/2 |
| 5,666,954 A | 9/1997 | Chapelon et al. | 600/439 |
| 5,720,286 A | 2/1998 | Chapelon et al. | 600/439 |
| 5,720,287 A | 2/1998 | Chapelon et al. | 600/439 |
| 5,769,790 A | 6/1998 | Watkins et al. | 600/439 |
| 5,817,021 A | 10/1998 | Reichenberger | 600/439 |
| 5,823,962 A | 10/1998 | Schaetzle et al. | 600/439 |
| 5,827,204 A | 10/1998 | Grandia et al. | 601/2 |
| 5,833,647 A | 11/1998 | Edwards | 604/22 |
| 5,873,828 A | 2/1999 | Fujio et al. | 600/439 |
| 5,895,356 A | 4/1999 | Andrus et al. | 600/439 |
| 5,993,389 A | 11/1999 | Driscoll, Jr. et al. | 600/371 |
| 6,007,499 A | 12/1999 | Martin et al. | 601/3 |
| 6,039,694 A | 3/2000 | Larson et al. | 600/459 |
| 6,050,943 A | 4/2000 | Slayton et al. | 600/439 |
| 6,179,831 B1 | 1/2001 | Bliweis | 606/21 |
| 6,221,015 B1 | 4/2001 | Yock | 600/439 |
| 6,267,734 B1 | 7/2001 | Ishibashi et al. | 601/2 |
| 6,409,720 B1 | 6/2002 | Hissong et al. | 606/27 |
| 6,425,867 B1 | 7/2002 | Vaezy et al. | 600/439 |
| 6,491,672 B2 | 12/2002 | Slepian et al. | 604/267 |
| 6,595,934 B1 | 7/2003 | Hissong et al. | 601/3 |
| 6,599,256 B1 | 7/2003 | Acker et al. | 601/2 |
| 6,633,658 B1 | 10/2003 | Dabney et al. | 382/128 |
| 6,656,136 B1 | 12/2003 | Weng et al. | 601/2 |
| 6,676,601 B1 | 1/2004 | Lacoste et al. | 600/439 |
| 6,685,639 B1 | 2/2004 | Wang et al. | 600/439 |
| 6,716,184 B2 | 4/2004 | Vaezy et al. | 601/3 |
| 6,719,699 B2 | 4/2004 | Smith | 600/459 |
| 6,846,291 B2 | 1/2005 | Smith et al. | 600/459 |
| 2002/0193681 A1 | 12/2002 | Vitek et al. | 600/411 |
| 2003/0069569 A1 | 4/2003 | Burdette et al. | 606/27 |
| 2003/0125623 A1 | 7/2003 | Kelly et al. | 600/437 |
| 2004/0019278 A1 | 1/2004 | Abend | 600/545 |
| 2004/0078034 A1 | 4/2004 | Acker et al. | 606/27 |
| 2004/0097805 A1 | 5/2004 | Verard et al. | 600/428 |
| 2004/0097840 A1 | 5/2004 | Holmer | 601/2 |
| 2004/0143186 A1 | 7/2004 | Anisimov et al. | 600/437 |
| 2004/0153126 A1 | 8/2004 | Okai | 607/1 |
| 2004/0181178 A1 | 9/2004 | Aldrich et al. | 601/3 |
| 2004/0234453 A1 | 11/2004 | Smith | 424/9.5 |

FOREIGN PATENT DOCUMENTS

| | | |
|---|---|---|
| EP | 01265223 B1 | 11/2002 |
| WO | WO 00/72919 | 12/2000 |

OTHER PUBLICATIONS

Bauer, A.; Solbiati, L.; Weissman, N. "Ultrasound Imaging with Sono Vue: Low Mechanical Index Real/time Imaging." *Acad Radiol* 2002, 9(suppl 2):S282/S284.

Brayman, Andrew A., Lizotte, Lynn M., Miller, Morton W. "Erosion of Artificial Endothelia In Vitro by Pulsed Ultrasound: Acoustic Pressure, Frequency, Membrane Orientation and Microbubble Contrast Agent Dependence." Ultrasound in Med. & Biol., vol. 25, No. 8, pp. 1305/1320, 1999. Copyright 1999 World Federation for Ultrasound in Medicine & Biology.

Chen, Wen/Shiang, et al. "A comparison of the fragmentation thresholds and inertial cavitation doses of different ultrasound contrast agents." J. Acoust. Soc. Am. 113 (1), Jan. 2003: pp. 643/651.

Chen, Wen/Shiang, et al. "Inertial Cavitation Dose and Hemolysis Produced in Vitro with or Without Optison." Ultrasound in me. & Biol., vol. 29, No. 5, pp. 725/737, 2003.

Dayton, Paul, A., et al. "The magnitude of radiation force on ultrasound contrast agents." J. Acoust. Soc. Am. 112 (5) Pt. 1, Nov. 2002: pp. 2183/2192.

Everbach, Carr, E. and Charles W. Francis. "Cavitational Mechanisms in Ultrasound/Accelerated Thrombolysis at 1 MHz." Ultrasound in Med. & Biol., vol. 26, No. 7, pp. 1153/1160, 2000. Copyright 2000 World Federation in Medicine and Biology.

Guzman, Hector R., et al. "Ultrasound—Mediated Disruption of Cell Membranes. I. Quantification of Molecular uptake and Cell Viability." J. Acoust. Soc. Am. 110 (1), Jul. 2001: pp. 588/595.

Guzman, Hector R., et al. "Ultrasound/mediated disruption of cell membranes. II. Heterogeneous effects on cells." J. Acoust. Soc. Am 110 (1), Jul. 2001: pp. 597/606.

Holt, Glynn, R., Roy, Ronald, A., Edson, Patrick A., Yang, Xinmai. "Bubbles and Hifu: the Good, the Bad and the Ugly." *Boston University, Department of Aerospace and Mechanical Engineering*, Boston, MA 02215: 120/131.

Hynynen, Kullervo, et al. "Potential Adverse Effects of High/Intensity Focused Ultrasound Exposure on Blood Vessels in Vivo." Ultrasound in Med. & Biol., vol. 22, No. 2, pp. 193/201, 1996.

Indman, Paul, MD,. "Alternatives in Gynecology." Hysteroscopy © 2000 OBGYN.net<http://www.gynalternatives.com/hsc.html>.

Ka/yun Ng, Yang Liu. "Therapeutic Ultrasound: Its Application in Drug Delivery." Medicinal Research Reviews, vol. 22, 204/223, 2002 © 2002 John Wiley & Sons, Inc.

Kaczkowski, Peter J., Vaezy, Shahram, Martin, Roy, Crum, Lawrence. "Development of a High Intensity Focused Ultrasound System for image/guided ultrasonic surgery." Ultrasound for Surgery 2001. <http://cimu.apl.washington.edu/hifusurgerysystem.html>.

Klibanov, Alexander L; Rasche, Peter T.; Hughes, Michael S.; Wojdyla, Jolette K.; Galen, Karen P.; Wiblee, James H.; Brandenburger, Gary H.. "Detection of Individual Microbubbles of an Ultrasound contrast Agent: Fundamental and Pulse Inversion Imaging[1]." *Acad Radiol* 2002, 9(suppl 2):S279/S281.

Miller, Morton W. et al. "A Review of In Vitro Bioeffects of Intertial Ultrasonic Cavitation From a mechanistic Perspective." Ultrasound in Med & Biol., vol. 22, No. 9, pp. 1131/1154, 1996.

Nobuki Kudo, Takehiro Miyaoka, Kengo Okada, and Katsuyuki Yamamoto. "Study on Mechanism of Cell Damage Caused by Microbubbles Exposed to Ultrasound." *Graduate School of Engineering, Hokkaido University*, Japan, *Research Institute for Electronic Science, Hokkaido University*, 060/0812 Japan.

Ostensen, Jonny, PhD; Bendiksen, Ragner, MSc. "Characterization and Use of Ultrasound Contrast Agents." *Acad Radiol* 2002; 9(suppl 2):S276/S278.

Owaki, T., nakano, S. Arimura, K., Aikou, T. "The Ultrasonic Coagulating and Cutting System Injuries Nerve Function." *First Department of Surgery, Kagoshima University School of Medicine*, Kagoshima, Japan, *Endoscopy*. (2002) 575/579.

Physicians. "Breast Cancer—Insightec: focused ultrasound for non invasive treatment." FAQ<http://www.exablate2000.com/physicians_faq.html>.

Poliachik, Sandra L., et al. "Activation, Aggregation and Adhesion of Platelets Exposed to High/Intensity Focused Ultrasound." Ultrasound in Med. & Biol., vol. 27, No. 11, pp. 1567/1576, 2001.

Poliachik, Sandra L., et al. "Effect of High—Intensity Focused Ultrasound on Whole Blood with or without Microbubble Contrast Agent." Ultrasound in Med. & Biol., vol. 25, No. 6, 1999: 991/998.

Porter, T.R., Xie, F. "Ultrasound, Microbubbles and Thrombolysis." Progress in Cardiovascular Diseases, vol. 44, No. 2, Oct. 2001: 101/110.

Rivens, I.H., Rowland, I.J., Denbow, M., Fisk, N.M., Harr, G.R., Leach, M.O. "Vascular occlusion using focused ultrasound surgery for use in fetal medicine." *European Journal of Ultrasound 9* (1999): 87/97.

Rosenschein, Uri, et al. "Ultrasound Imaging/Guided Nonivasive Ultrasound Thrombolysis/Preclinical Results." © American Heart Association, Inc. (Circulation. 2000;102:238/245.) <http://www.circulationaha.com.org>.

Rosenschein, Uri, et al. "Shock/Wave Thrombus Ablation, A New Method for Noninvasive Mechanical Thrombolysis." The American Journal of Cardiology, vol. 70, Issue 15, Nov. 1992: pp. 1358/1361.

Tachibana, Katsuro and Shunro MD., PhD. "The Use of Ultrasound for Drug Delivery." First Department of Anatomy, Fukuoka University School of Medicine, Nanakuma, Japan,Echocardiography. (2001) 323/328.

Tachibana, Katsuro, and Shunro M.D., Ph.D. "Albumin Microbubble Echo/Contrast Material as an Enhancer for Ultrasound Accelerated Thrombolysis." (Circulation, 1995; 92: 1148/1150.) © 1995 American Heart Association, Inc.

Tardy, I.; Pochon, S.; Theraulaz, P. Nanjappan; Schneider, M. "In Vivo Ultrasound Imaging of Thrombi Using a Target/specific Contrast Agent[1]." Acad Radiol 2002, 9(suppl 2):S294/S296.

Vaezy, Shahram et al. 2001. "Acoustic surgery." Physics World (August): 35/39.

Vaezy, Shahram et al. 2001. "Experimental Investigations and Device Development." First International Workshop on the Application of HIFU in Medicine. (May 10/13): 4pp.

Watkin, Kenneth L., PhD; McDonald, Michael A., BS. "Multi/Modal Contrast Agents: A First Step[1]." Acad Radiol 2002, 9(suppl 2):S285/S287.

Watkin, Kenneth L., PhD; McDonald, Michael A., BS. "Schematic of the Tube, Cross Section Ultrasound Images of the Tube With Different Contrast Media (CM)." Acad Radiol 2002, 9(suppl 2):S288/S289.

Wickline, Samuel A., MD; Hughes, Michael, PhD; Ngo, Francis C., MD; Hall, Christopher, S., PhD; Marsh, Jon, N., PhD; Brown, Peggy A; Allen, John S., BS; McLean, Mark D.; Scott, Michael J., BS; Fuhrhop, Ralph W.; Lanza, Gregory M., MD, PhD. "Blood Contrast Enhancement with a Novel, Non/Gaseous Nanoparticle Contrast Agent[1]," Acad Radiol 2002, 9(suppl 2):S290-S293.

Anand, Ajay et al. "Using the ATL 1000 to Collect Domodulated RF Data for Monitoring HIFU Lesion Formation." Center for Industrial and Medical Ultrasound, University of Washington, Abstract. 11pp.

Hatangadi, Ram Bansidhar. "A Novel Dual Axis Multiplanar Transesophageal Ultrasound Probe for Three-Dimensional Echocardiograph."University of Washington, Department of Sciences and Engineering. (1994), Abstract. vol. 55-11B: 1pg.

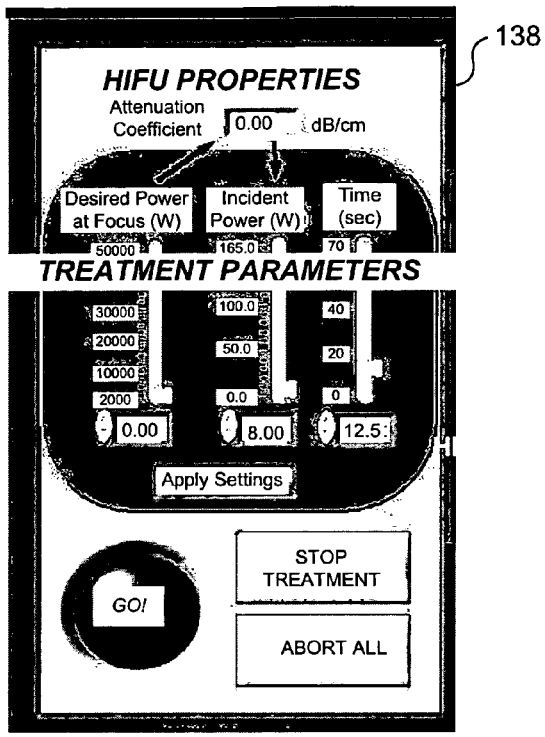
*FIG. 9A*
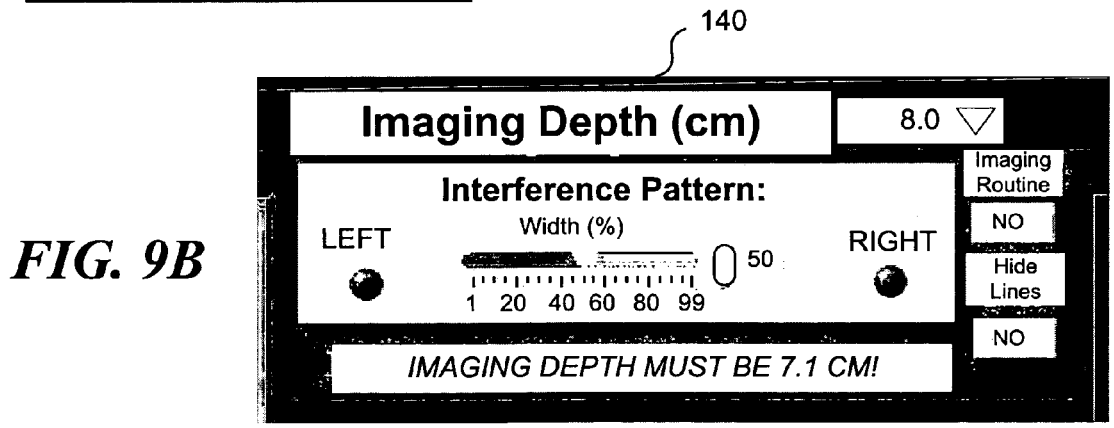
*FIG. 9B*
*FIG. 9C*
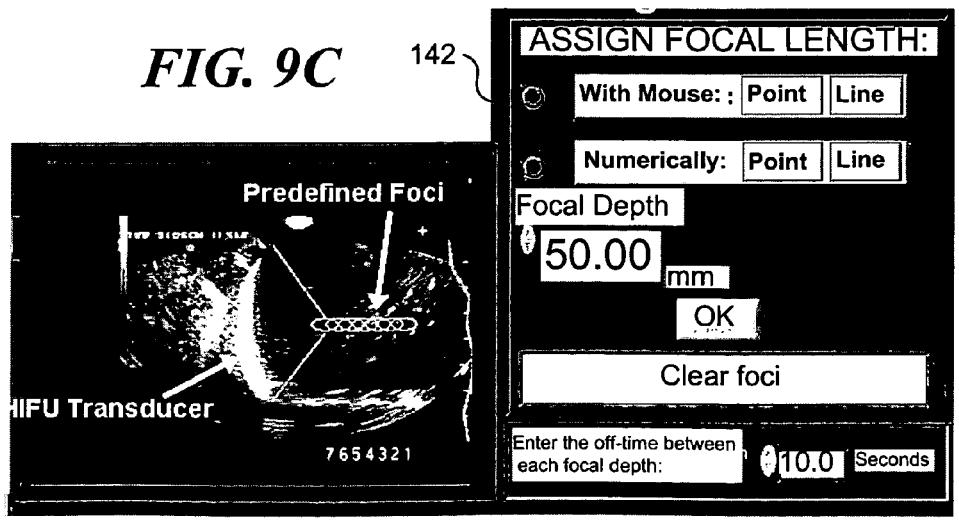

US 7,670,291 B2

INTERFERENCE-FREE ULTRASOUND IMAGING DURING HIFU THERAPY, USING SOFTWARE TOOLS

RELATED APPLICATIONS

This application is based on a prior copending provisional application, Ser. No. 60/610,456, filed on Sep. 16, 2004, the benefit of the filing date of which is hereby claimed under 35 U.S.C. §119(e).

GOVERNMENT RIGHTS

This invention was made with U.S. Government support under grant No. NGT5-40084/US#67-0242 awarded by NASA, under grant No. DAMD17-02-0014 awarded by the U.S. Army MRMC through the University of Mississippi NCPA, and under grant No. BES-002932 awarded by the National Science Foundation. The U.S. Government has certain rights in the invention.

BACKGROUND

Acoustic therapies include shock wave lithotripsy (SWL), high intensity focused ultrasound (HIFU), and ultrasound-enhanced drug delivery. HIFU is used for many therapeutic applications, including hemostasis, tumor treatment, and tissue necrosis. These procedures are made possible by the unique ability of such acoustic therapy technologies to selectively apply relatively large amounts of therapeutic energy (on the order of 1000 $W/cm^2$) to a treatment volume disposed deep within a body mass, without adversely affecting tissue disposed between an acoustic therapy transducer that produces the energy and the treatment volume. HIFU, in particular, is a powerful medical technique with great potential and is currently being employed, both in the United States and abroad, to treat tumors. However, to safely implement non-invasive, HIFU-based transcutaneous acoustic surgery, a medical imaging modality must be used to visualize the internal treatment site, for targeting the site and monitoring the treatment process. Ultrasound imaging is an attractive modality for the following reasons: (a) images are available in real-time; (b) portable imagers are commercially available; (c) Doppler-based imaging modalities can be used to detect bleeding; (d) ultrasound imaging is a relatively ubiquitous medical technology that is commonly available in medical facilities; and, (e) ultrasound imaging is relatively inexpensive, compared to other medical imaging systems, such as magnetic resonance imaging (MRI).

A problem with combining HIFU therapy with ultrasound imaging is that the high energy therapeutic waves introduces a significant amount of noise into an ultrasound imaging signal employed to monitor the treatment site, making simultaneous imaging and treatment difficult. Indeed, the high energy of the HIFU wave can completely overwhelm conventional ultrasonic imaging systems. One analogy that might help to make this problem clear relates to relative intensities of light. Consider the light coming from a star in the evening sky to be analogous to the low power imaging ultrasound waves that are reflected from a target area toward the imaging transducer, while the light from the sun is analogous to the HIFU waves generated by the therapy transducer. When the sun is out, the light from the stars is completely overwhelmed by the light from the sun, and a person looking into the sky is unable to see any stars, because the bright light from the sun completely masks the dim light coming from the stars. Similarly, the HIFU waves emitted by the therapy transducer completely overwhelm the lower energy imaging ultrasound waves produced by the imaging transducer, and any ultrasonic image generated is saturated with noise caused by the HIFU wave from the therapeutic transducer.

FIG. 1A schematically illustrates a prior art ultrasound image 10 in which a scanned field 12 is completely obscured by noise 14, caused by the simultaneous operation of an ultrasound imaging pulse (i.e., an ultrasound imaging wave) and a HIFU wave (neither shown). In ultrasound image 10, a clinician may be attempting to focus the HIFU wave on a treatment site 18. However, because noise 14 completely saturates scanned field 12, it is impossible to accurately focus the HIFU wave onto treatment site 18. If the therapy transducer is completely de-energized, noise 14 is eliminated from the scanned field. However, under these conditions, the focal point of the HIFU wave will not be seen, and thus, the HIFU wave cannot be accurately focused on treatment site 18. While some change in echogenicity at the HIFU focal point may persist for a time even after the HIFU wave is no longer active, any change in a position of the therapy transducer (or treatment site 18) will not register until the therapeutic transducer is re-energized. Thus, the HIFU wave cannot be focused in real time.

Some prior art systems have included a targeting icon in an ultrasound image to indicate where the known focal point of a specific HIFU transducer would be located in a scanned image. While this icon may be helpful in determining a position of the focal region of the HIFU transducer relative to the scanned ultrasound image, such an icon-based technique does not enable a clinician to observe real-time results. Once the HIFU therapeutic transducer is energized, the scanned ultrasound image is completely saturated with noise, and the clinician cannot monitor the progress of the treatment without again de-energizing the HIFU therapeutic transducer. Furthermore, it should be noted that the accuracy of such icon-based targeting systems generally degrades during treatment due to changes in refraction, temperature of the tissue, the presence of bubbles in or near the target area, and patient movement (including movement associated with respiration).

FIG. 1B schematically illustrates a prior art technique disclosed in U.S. Pat. No. 6,425,867 (the disclosure, specification, and drawings of which are hereby specifically incorporated herein by reference) for reducing the amount of noise disrupting an ultrasound image during HIFU therapy. In FIG. 1B, the HIFU wave generated by the therapeutic transducer has been pulsed. This technique produces an ultrasound image 20, in which the location of noise 24 in a scanned field 22 is a function of the interference between the pulsed HIFU wave generated by the therapy transducer and the ultrasonic imaging pulses generated by the scanning transducer. In FIG. 1B, noise 24 substantially masks a treatment site 28. This result would not occur in all cases, because to an observer, noise 24 would move across scanned field 22 as the interference between the HIFU waves and the imaging pulses varies in time. Pulsing of the HIFU wave alone would thus enable the clinician to view a noise-free image of the treatment site only when noise 24 was randomly shifted to a different part of scanned field 22, away from the treatment site. However, such pulsing alone generates an image that is extremely distracting to a clinician, because noise 24 flickers across scanned field 22, making it difficult to concentrate and difficult to consistently determine where the focal point of the HIFU wave is, relative to the treatment site, in real time.

FIG. 1C schematically illustrates another prior art technique that is disclosed in U.S. Pat. No. 6,425,867 (referred to hereafter as the '867 patent), also for reducing the amount of noise disrupting an ultrasound image during HIFU therapy. In an ultrasound image 30, a HIFU wave from a therapy transducer has been both pulsed and synchronized with respect to the ultrasonic imaging pulses from an imaging transducer, to ensure that noise 34 does not obscure a treatment site 38. In ultrasound image 30, noise 34 has been shifted to a location within a scanned field 32 that is spaced apart from treatment site 38, by selectively adjusting both the pulsing and the synchronization of the HIFU wave. Preferably, noise 34 is shifted completely away from treatment site 38, thus providing the clinician a noise-free, stable image of treatment site 38 that clearly shows the location of the focal point of the HIFU wave relative to the treatment site. Thus, the HIFU wave can be focused onto treatment site 38, in real time. By synchronizing the HIFU bursts within each imaging frame, the interference can be relegated to certain portions of the image, such as a fringe of the ultrasound image, enabling other portions of the ultrasound image to remain useful for monitoring and guidance. If the imaging process and the HIFU bursts are not synchronized, the interference will randomly obscure the treatment site, generally as indicated in the example of FIG. 1B.

FIG. 2 is a block diagram from the '867 patent, schematically illustrating a system that synchronizes the ultrasound image and HIFU waves required for the simultaneous imaging and therapy in real time. A conventional imaging probe 44 is connected to an ultrasound imaging machine 40 via a cable 42. Imaging probe 44 generates ultrasonic imaging pulses that propagate to the target area, are reflected from structure and tissue within the body, and are received by the imaging probe. The signal produced by the imaging probe in response to the reflected ultrasound imaging waves is communicated to the ultrasound imaging machine through cable 42 and processed to provide a visual representation of the structure and tissue that reflected the ultrasonic imaging pulses. An imaging beam sector 46 from imaging probe 44 is identified in the Figure by dash lines. The system described in the '867 patent also includes a therapeutic transducer 60. When excited, this therapeutic transducer generates HIFU waves that are focused at a particular point of interest, i.e., a treatment site within a patient's body. In FIG. 2, the path of a HIFU beam 62 (indicated by solid lines to the right of therapeutic transducer 60) narrows to a focal point 64.

Synchronization output signal 48 is supplied to a synchronization delay 50, which enables the user to selectively vary the initiation of each HIFU wave with respect to each sequence of ultrasonic imaging pulses that are generated to form an ultrasonic image. Referring to FIG. 1C, delay 50 enables a user to vary the position of noise 34 in scanned field 32, so that the noise is moved away from treatment site 38, to a different portion of scanned field 32. A HIFU duration circuit 52 is used to control the duration of the HIFU wave. A longer duration HIFU wave will apply more energy to the treatment site. If the duration of the HIFU wave is too long, the duration of noise 34 as shown in ultrasound image 30 will increase and can extend into the next ultrasound imaging pulse to obscure treatment site 38, or may completely obscure ultrasound image 30, generating a display similar to ultrasound image 10 in FIG. 1A. Thus, the user will have to selectively (i.e., manually) adjust HIFU duration circuit 52 to obtain a noise-free image of treatment site 38, while providing a sufficient level of energy to the treatment site to achieve the desired therapeutic effect in an acceptable time. A HIFU excitation frequency generator 56 is used to generate the desired frequency for the HIFU wave, and a power amplifier 58 is used to amplify the signal produced by the HIFU excitation frequency generator to achieve the desired energy level of the HIFU wave. Power amplifier 58 is thus adjustable to obtain a desired energy level for the HIFU wave.

Significantly, the system disclosed in the '867 patent requires modifying a conventional ultrasound imaging machine to achieve modified ultrasound imaging machine 40, which is capable of providing synchronization output signal 48. The '867 patent notes that such a synchronization output signal is not normally provided in prior art conventional ultrasound imaging machines. The '867 patent suggests that if an ultrasound imaging machine capable of providing the synchronization output signal is not available, then a synchronization output signal can be derived from the ultrasound imaging signals conveyed by cable 42. The '867 patent also suggests that an optional stable synchronization signal generator 66 can be used to synchronize the HIFU wave to the imaging ultrasonic wave, instead of using synchronization output signal 48 from ultrasound imaging machine 40. Stable synchronization signal generator 66 can be used to provide a stable synchronizing pulse to initiate the HIFU wave, and the timing of this stable synchronizing pulse can be manually varied until a noise-free image of the treatment site has been obtained.

Essentially, the '867 patent addresses HIFU interference of ultrasound imaging by synchronizing the interference so that the interference is stable and is located at the fringes of the image. As a result, the region of interest in the image is not obscured (like the condition that is schematically indicated in FIG. 1C). This functionality requires knowledge of the frame rate and phase of the imaging cycle, both of which vary with changes to user control settings (particularly depth and switching modality from b-mode to Doppler). Once the frame rate and phase are known, HIFU can be gated synchronously with the imaging cycle and the interference that is caused can be moved to the fringes of the image. Unfortunately, there is no simple way of determining the frame rate and phase of a stand-alone commercial imager that has not been designed to provide such information (i.e., which has not been modified to provide synchronization output signal 48).

As indicated in the '867 patent, ultrasound imaging systems can be designed to incorporate a synchronization output signal. However, even though ultrasound imaging systems are significantly less expensive than MRI imaging systems, high end ultrasound imaging systems can still cost in excess of $150,000, and it would be desirable to provide a synchronization technique that is compatible with ultrasound imaging systems that do not provide a synchronization output signal (the majority of ultrasound imaging systems sold do not provide any signal corresponding to the synchronization output signal described in the '867 patent). The '867 patent also suggests that the synchronization signal (frame rate without phase information) could be obtained from the cable coupling an ultrasound imaging probe to ultrasound imaging machines. This theoretically could be achieved by detecting current in the cable. However, such cables include many wires conducting various different electrical currents, and these cables are well shielded to meet safety and radio frequency interference standards. Hence, obtaining the signal necessary for synchronization from a shielded cable is generally a challenging task. The cable could be modified to facilitate extraction of the synchronization signal; however, such a modification is not likely to be supported by the manufacturers of the ultrasound imaging equipment, and operators of medical equipment are unlikely to pursue a modification not sanctioned by a manufacturer, particularly because of the potential liability and loss of warranty concerns. Furthermore, both the use of synchronization signal generator 66 and synchronization output signal 48 simply shift the interference generated by the HIFU waves from one portion of the ultrasound image to another. While this shift does enable a region of interest in the image to be interference-free, the interference still exists in other portions of the image displayed to the user.

Thus, it would be desirable to provide a technique for achieving an interference-free ultrasound image in the presence of non-imaging ultrasound waves, such as HIFU. It would further be desirable that such an interference-free ultrasound image be achievable without modifying a conventional ultrasound imaging apparatus to provide a synchronization signal.

SUMMARY

Disclosed herein is a technique for using image-processing software to manipulate data obtained from an ultrasound imaging system to remove noise generated by non-ultrasound imaging ultrasound sources, such as a HIFU therapy transducer. This image processing technique does not require modification of the ultrasound imaging system and enables a therapeutic ultrasound transducer to be energized for longer periods of time, thereby reducing the overall treatment time required. Rather than using a synchronization signal that is obtained from the ultrasound imaging system to control the therapeutic ultrasound transducer, the therapeutic ultrasound transducer is simply controlled to ensure that the frequency of the therapy waves are different than a frequency of imaging waves. This difference in frequencies is used to achieve an image, as discussed above with respect to FIG. 1B, where the interference moves across the ultrasound image over time. However, as disclosed herein, unlike the previous approach, further processing of the ultrasound image occurs before it is displayed to a user, such that the interference flickering across the image as in FIG. 1B is eliminated from the image displayed to the user.

In this new approach, ultrasound image frames captured by an ultrasound imaging system are sent to a processor before being displayed to the user. The processor is configured to analyze each frame to identify interference-free portions of the frame. The interference-free portions of the frames are saved, and combined with other interference-free portions of other frames until a composite interference-free ultrasound image can be displayed to the user. This method will have the effect of reducing a frame rate that can be displayed to user; however, empirical testing has indicated that a useful, interference-free ultrasound image, at an acceptable frame rate, can be obtained under a variety of operating conditions.

In one embodiment, both the ultrasound imaging system and the therapeutic ultrasound transducer are triggered from a common external trigger (the common external trigger preferably being implemented using a function generator and a set of pulse generators). The external trigger can be controlled such that the interference from the therapeutic ultrasound transducer sweeps across the ultrasound imaging frames, generally as indicated in FIG. 1B, as discussed above.

In another embodiment, the ultrasound imaging system is triggered independently, and the frequency of the square wave used to induce a HIFU duty cycle is varied until the interference from the HIFU sweeps across the ultrasound imaging frames, generally as indicated in FIG. 1B.

The processor analyzes each ultrasound image frame by separating the frame into a plurality of slices. For each slice, a region of interest is selected from the slice for further analysis. Preferably, about 10% of the slice is selected for further analysis, and more preferably, the region of interest selected comes from a lower portion of the slice, where interference is most likely to occur. Statistical values for pixel intensities are calculated for the region of interest. Based on the statistical values, a determination is made as to whether the region of interest includes interference, or is interference-free. Note that pixel intensity values for interference can be readily distinguished from pixel intensity values from a normal image that is free of interference, because of the relatively uniformly high pixel intensity values associated with interference. Based on this analysis, interference-free slices are saved, and slices including interference are discarded. A plurality of frames are processed until a composite interference-free ultrasound image can be obtained.

Preferably, once a slice is saved, the processor discards any slices corresponding to the same region, until an entire interference-free image is obtained; the algorithm then starts over, to generate another composite interference-free ultrasound image. This prevents the same slice from being introduced more than once into the composite images, which would produce inaccurately bright pixels. In some embodiments, a signal is sent to the ultrasound imaging system such that the ultrasound imaging system does not further interrogate regions for which a slice has been saved.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIGS. 1A-1C (all Prior Art) respectively illustrate ultrasonic images generated during the simultaneous use of ultrasound for imaging and therapy, the pulsing of the HIFU in a conventional scanned image, and the synchronized pulsing of the HIFU and the scan image so as to shift the noise away from a displayed treatment site;

Figure 3A:
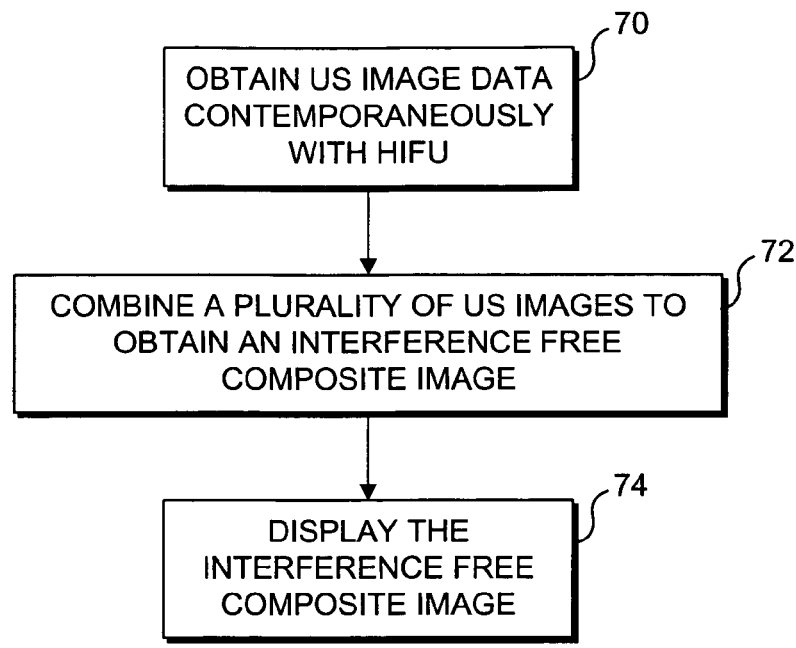
FIG. 3A is a high level flowchart of an exemplary technique for generating a composite interference-free ultrasound image when non-imaging ultrasound waves (such as HIFU) are present.
Figure 3B:
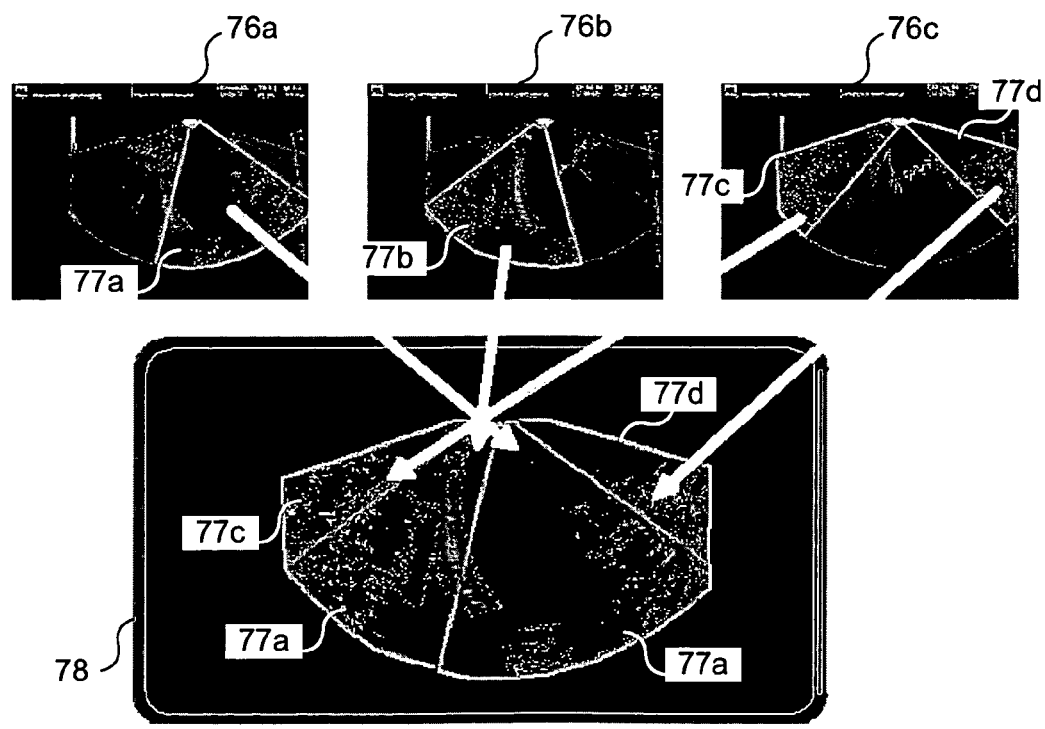
Figure 4A:
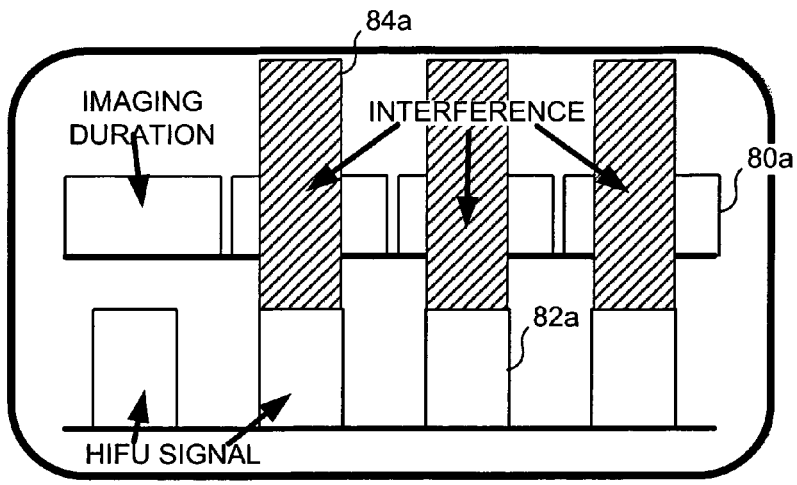
Figure 4B:
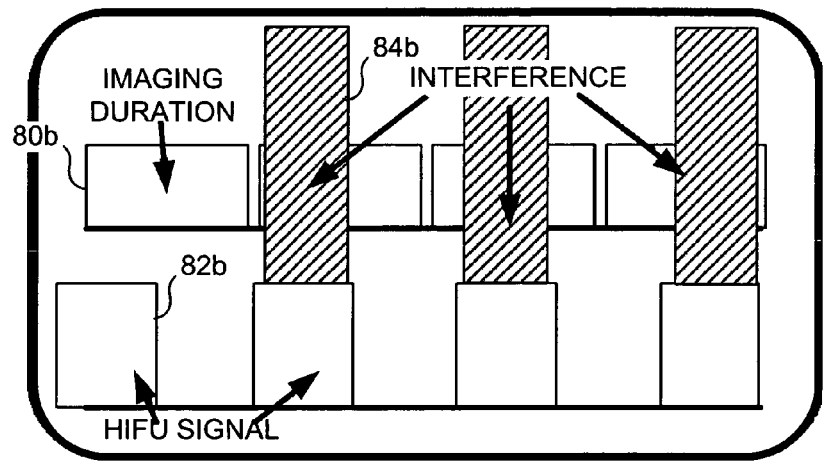
Figure 4C:
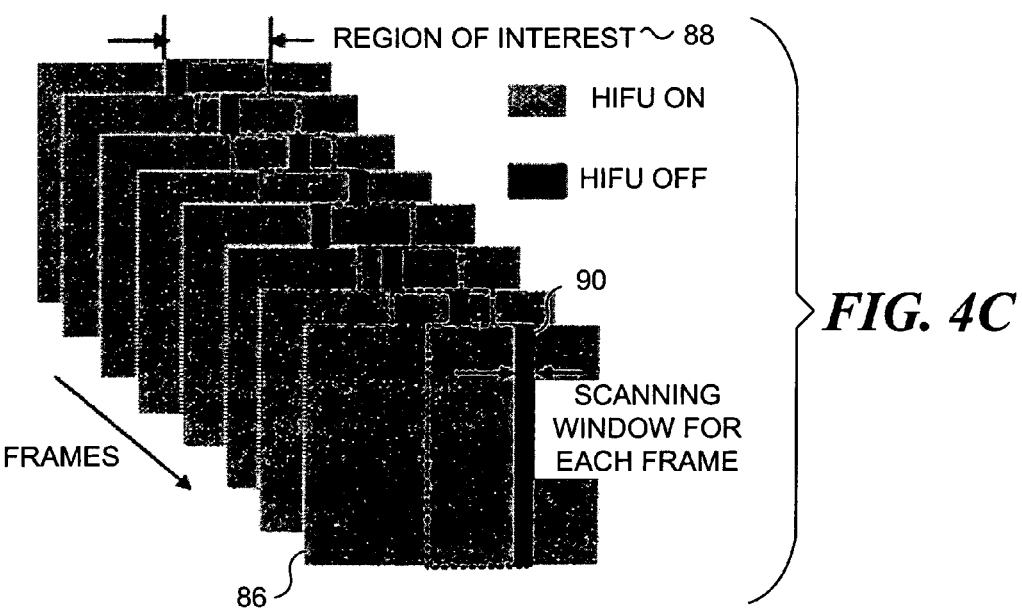
Figure 5A:
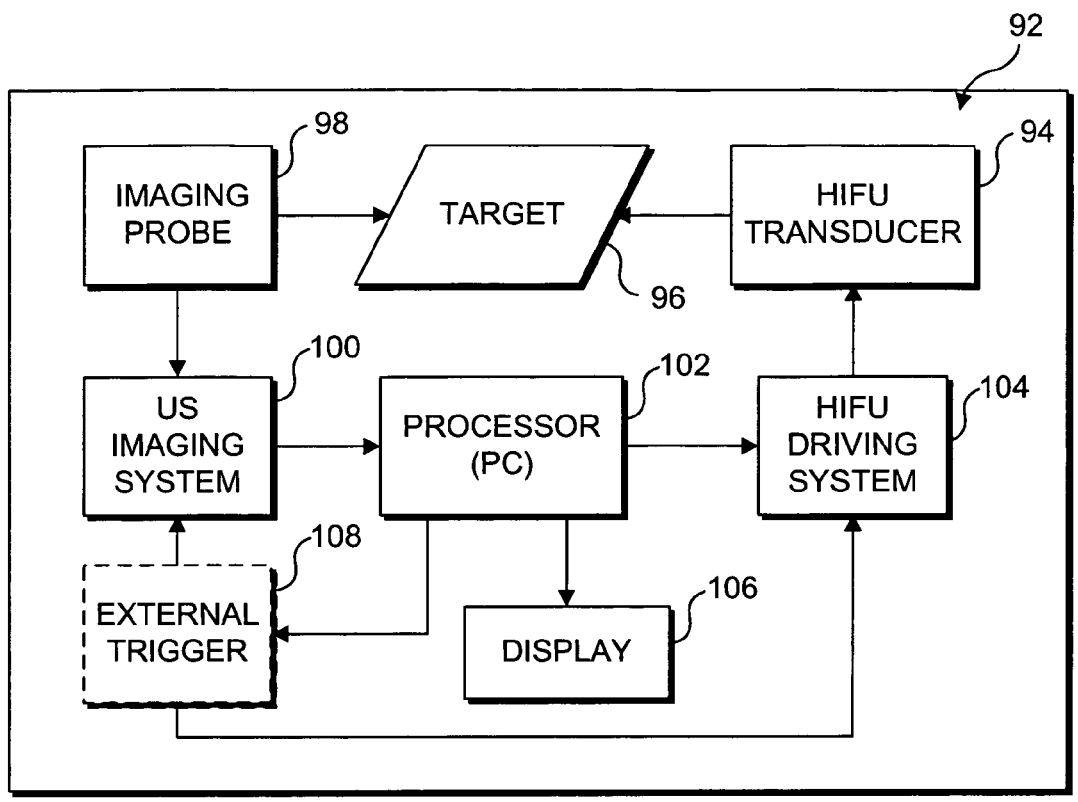
Figure 5B:
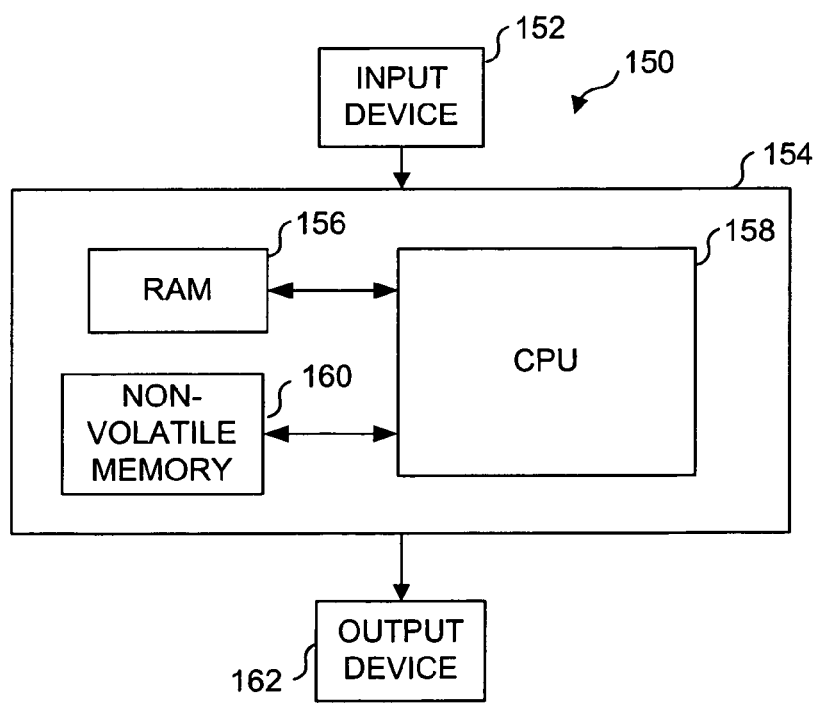
Figure 6:
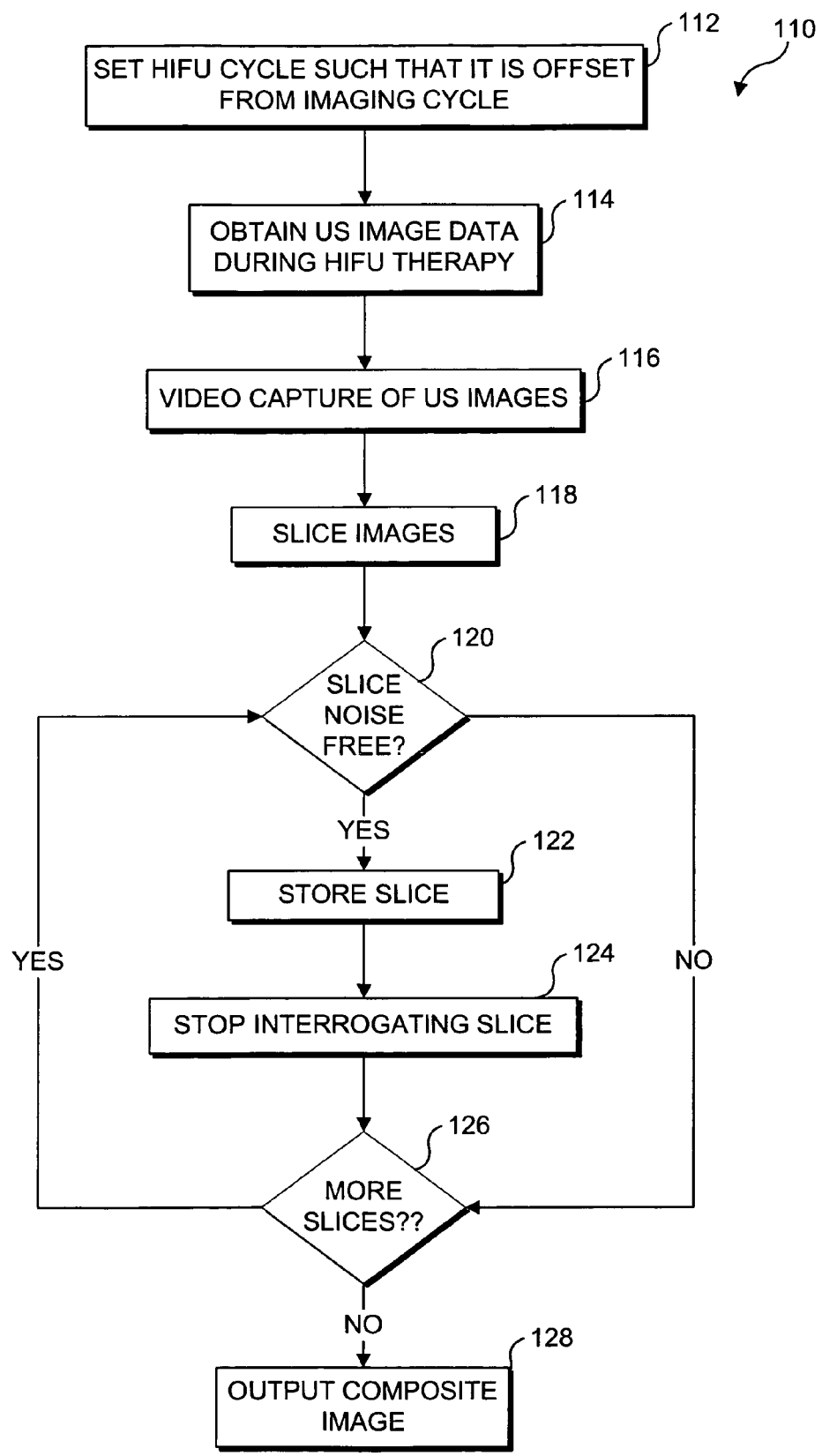
Figure 7:
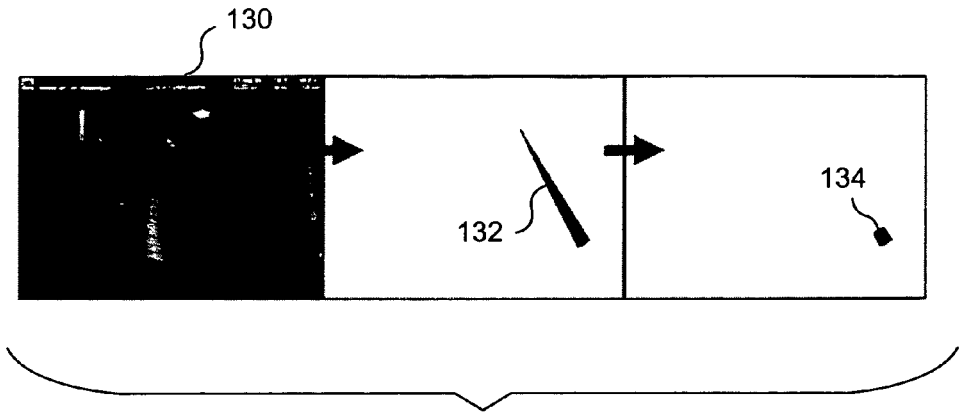
Figure 8:
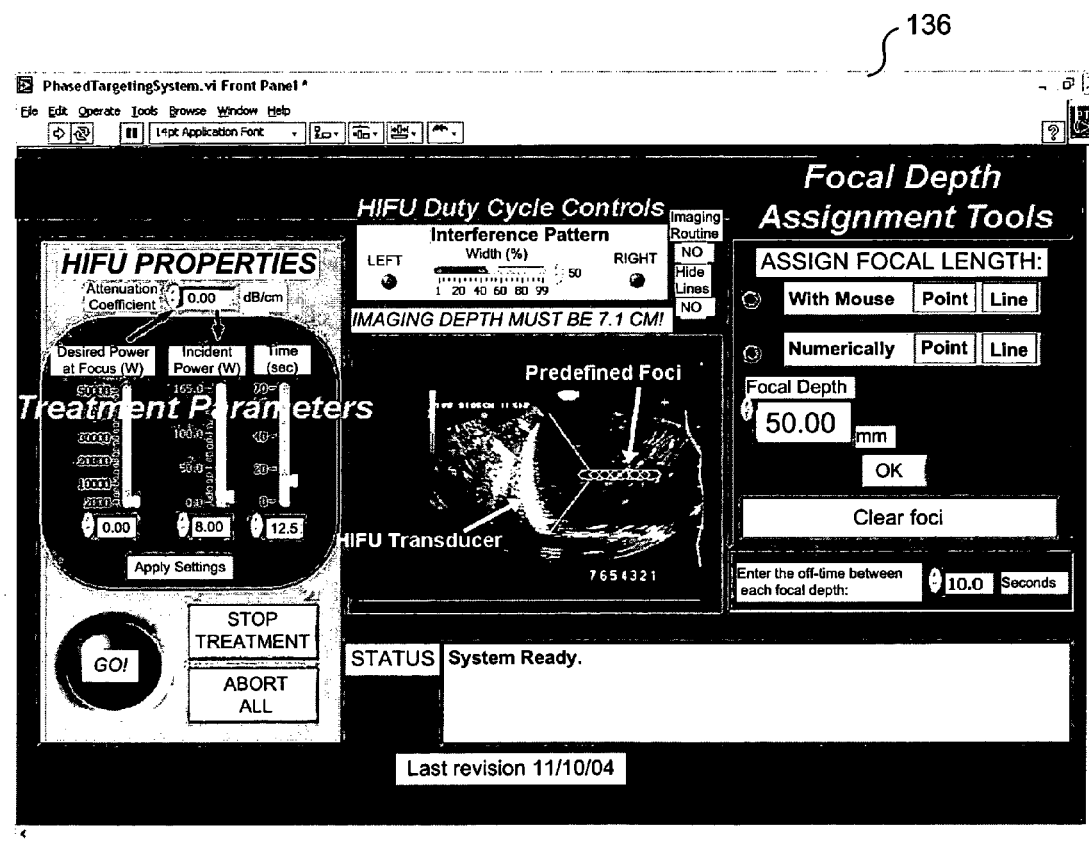
Figure 10A:
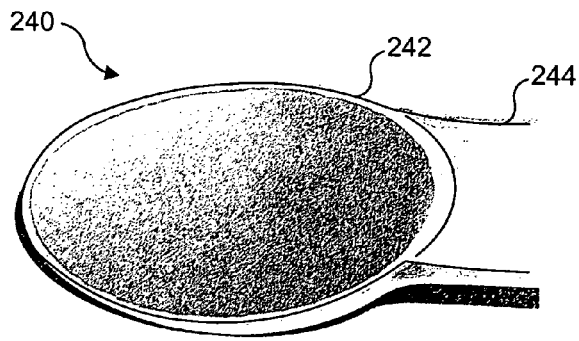
Figure 10B:
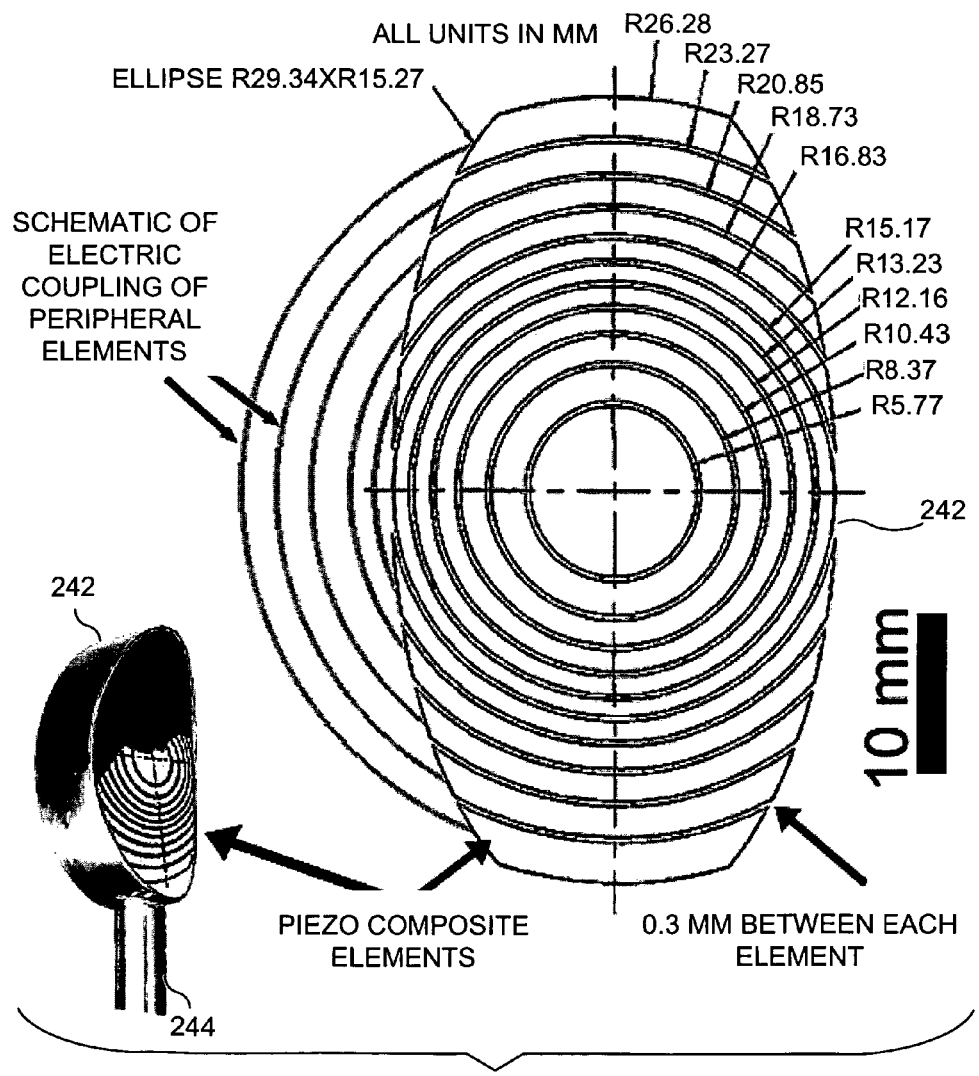

FIG. 3B graphically illustrates how three ultrasound images including interference can be combined to achieve a single composite interference-free ultrasound image;

FIG. 4A (Prior Art) schematically illustrates how an earlier system for synchronizing HIFU therapy with ultrasound imaging synchronized the HIFU waves and ultrasound imaging waves such that the interference due to the HIFU waves consistently appeared in the same position in each ultrasound image frame;

FIG. 4B schematically illustrates how the technique described herein ensures that the non-imaging ultrasound waves (e.g., HIFU) and ultrasound imaging waves are offset, such that the interference due to the non-imaging ultrasound waves does not appear in the same position in each ultrasound image frame;

FIG. 4C schematically illustrates how a noise-free portion of an ultrasound image shifts across a plurality of frames, and how a region of interest in the ultrasound frames can be narrowed to achieve a higher frame rate;

FIG. 5A is a block diagram illustrating a system for generating a composite interference-free ultrasound image from a plurality of ultrasound images that include both interference and interference-free portions;

FIG. 5B schematically illustrates an exemplary computing system used to implement the method of FIG. 3A;

FIG. 6 is a more detailed flowchart of the steps used to implement the technique of FIG. 3A, for generating a composite interference-free ultrasound image when non-imaging ultrasound waves (such as HIFU) are present;

FIG. 7 schematically illustrates how the slicing step of the FIG. 6 can be implemented;

FIG. 8 is an image of an exemplary user interface that can be employed to implement the method of FIG. 3A;

FIGS. 9A-9C are enlarged images of selected portions of the exemplary user interface of FIG. 8;

FIG. 10A schematically illustrates an exemplary HIFU therapy probe including a phased array transducer that can be controlled using the user interface of FIG. 8;

FIG. 10BB illustrates additional details for the structure of the phased array transducer of FIG. 10A.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive.

The terms "therapeutic transducer," "HIFU transducer," and "high intensity transducer," as used herein and in the claims that follow all refer to a transducer that is capable of being energized to produce ultrasonic waves that are much more energetic than the ultrasonic waves produced by an imaging transducer, and which can be focused or directed onto a discrete location, such as a treatment site in a target area. The term "HIFU beam" should be understood to refer to a characteristic pattern of HIFU waves emitted from a HIFU transducer. Ultrasound is a wave-based phenomenon; however, those of ordinary skill in the art often refer to HIFU waves as a "beam," much in the way the science of optics refers to light as a beam, even though light exhibits aspects of both waves and particles. This dual nature is particularly true with respect to HIFU waves, because HIFU waves can be focused in much the same way that light can be focused (i.e., a focal point of a lens or phased array is associated with HIFU waves, and the focal point corresponds to a region where the HIFU waves are focused so that they are able to deliver a maximum amount of acoustic energy).

As explained above, a major challenge in real-time ultrasound guidance and monitoring of HIFU therapy is the interference of the HIFU signal with the imaging system. Previously, simultaneous imaging and therapy has been performed by synchronizing bursts of therapy signals with the imaging signals by using a trigger from the imaging system to limit the interference region to an area of the image outside the treatment site (as discussed above with respect to FIGS. 1A, 1B, 1C, and 2). A drawback of such an approach is that the imaging field of view is limited (i.e., at least some portion of the image is obscured by interference, even though the interference can be shifted away from a particularly important region of interest), and the overall treatment time is longer than it would be without such synchronization, because the therapy is intermittent (with typical duty cycles of 50-70%). An additional drawback, discussed above, is that a modification of the imaging system hardware is typically required to obtain the synchronization trigger. The method disclosed herein is a software-based technique for obtaining an interference-free ultrasound image in the presence of HIFU (or other non-imaging ultrasound waves), by combining multiple interference-free regions from a plurality of ultrasound images using image processing, thus providing an enhanced field of view for imaging a treatment site. The enhanced field of view can potentially enable monitoring of undesired therapeutic effects away from the treatment site, e.g., due to the presence of bone or air interfaces. Note that because the synchronization technique discussed above in detail obscures at least part of the image, such undesirable effects can remain unobserved using the prior synchronization technique (i.e., evidence of such undesirable effects can be obscured by the interference). The techniques disclosed herein can also allow better real-time monitoring of lesion migration outside the intended treatment site. An additional advantage provided by the present technique is that a requirement for hardwired synchronization between the therapy and imaging systems is avoided. Yet another advantage of the present technique is that the HIFU duty cycle can be increased without sacrificing the field of view of the treatment site, thus reducing the overall treatment time, especially for large treatment volumes.

FIG. 3A is a high level flowchart of an exemplary technique for generating a composite interference-free ultrasound image when non-imaging ultrasound waves (such as HIFU) are present. In a step 70, ultrasound image data are obtained contemporaneously with HIFU therapy, or some other form of non-imaging ultrasound. While the techniques disclose herein are particularly well-suited to simultaneous ultrasound imaging and HIFU therapy, it should be recognized that such techniques can also be used to achieve an interference-free composite image in the presence of other types of non-imaging ultrasound waves that would otherwise at least partially interfere with a view of a site. In a step 72, the raw ultrasound images (i.e., a plurality of ultrasound image frames) are processed to obtain an interference-free composite image. In this step, interference-free portions are selected from a plurality of image frames and are combined to achieve the composite image. In a step 74, the interference-free composite image is displayed.

Figure 1A:
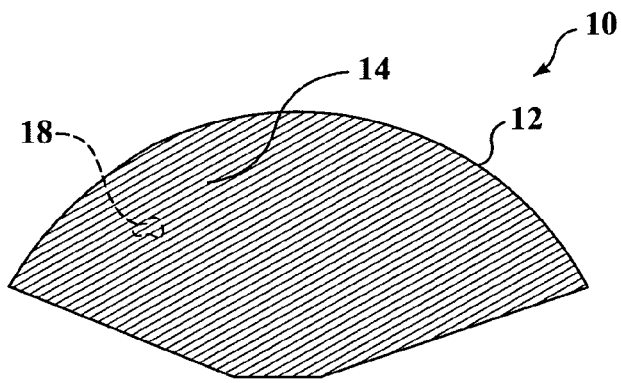
Figure 1B:
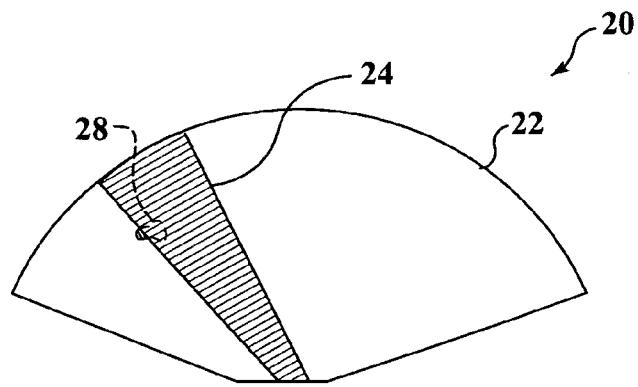
Figure 1C:
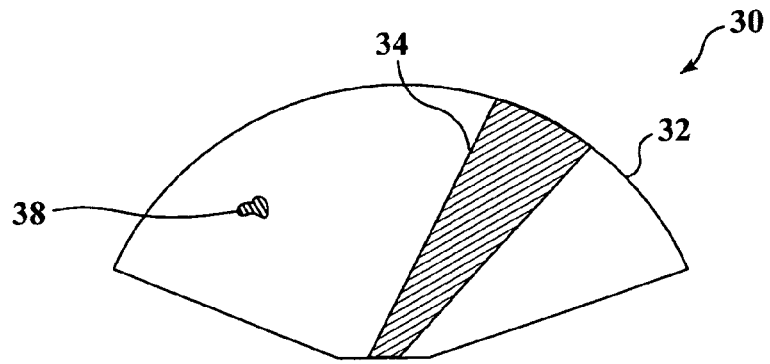
Figure 2:
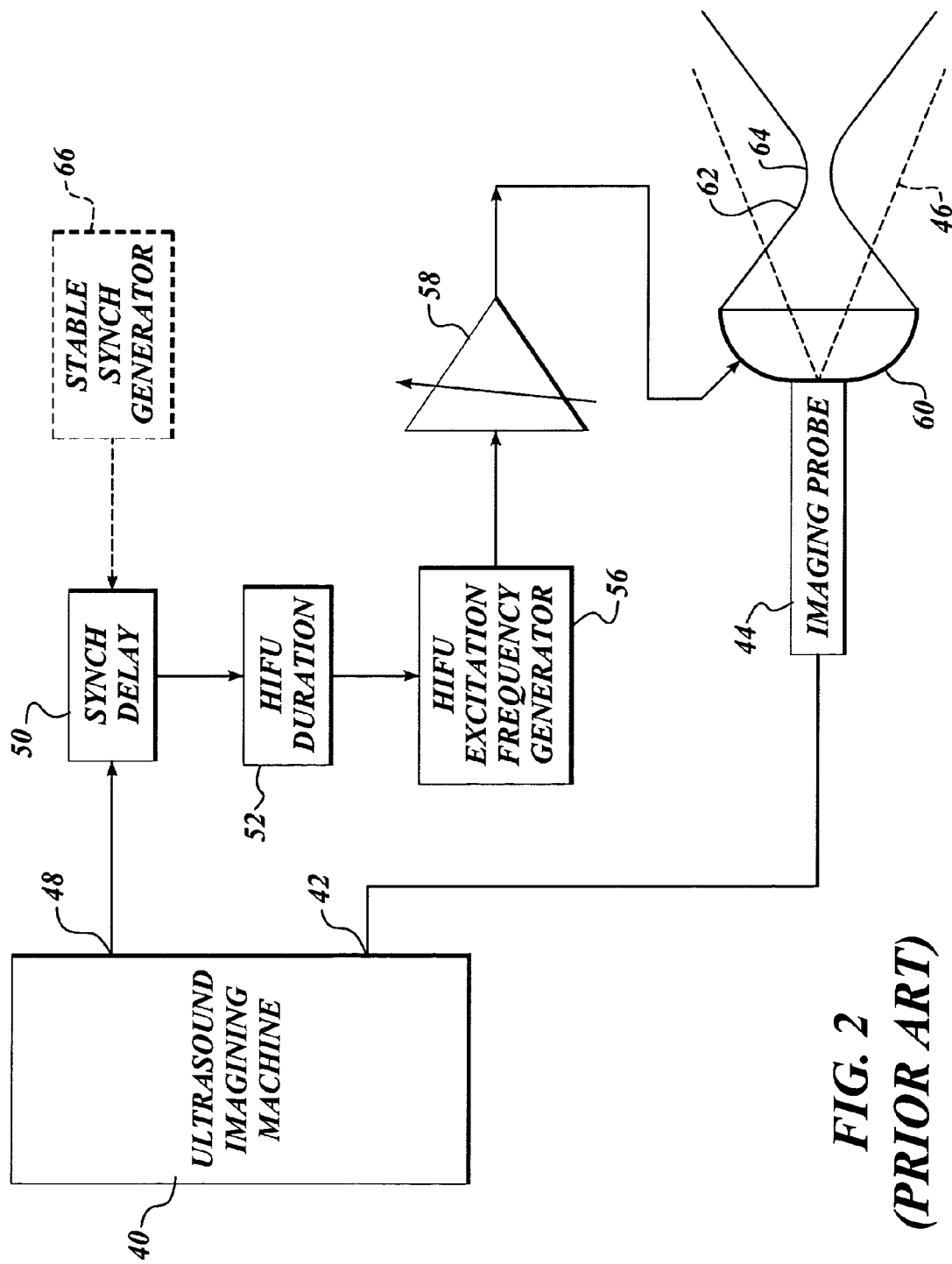
FIG. 2 (Prior Art) is a block diagram illustrating the components of an earlier system that is capable of synchronizing HIFU therapy in ultrasound imaging, which requires the modification of commercially available ultrasound imaging equipment to achieve a synchronization signal.

FIG. 3B graphically illustrates how three ultrasound images including both interference-free portions and interference can be processed to achieve a single composite interference-free ultrasound image. An ultrasound image frame 76a includes an interference-free portion 77a. An ultrasound image frame 76b includes an interference-free portion 77b. An ultrasound image frame 76c includes interference-free portions 77c and 77d. Image processing techniques can be used to combine interference-free portions 77a-77d to achieve a composite interference-free image 78. Note that the entire imaging field of view can be reconstructed by overlapping an integer number (k) of scanning windows if the repetition period of the HIFU signal matches the duration of each imaging frame and if the "HIFU on time" is an integer multiple (k) of the HIFU off time. Compare composite image 78 to FIG. 1C, and it will be evident that the entire field of view is clearly visible in composite image 78, while a portion of the field of view in FIG. 1C is still obscured, despite the synchronization described in the '867 patent.

FIG. 4A (Prior Art) schematically illustrates how an earlier system for synchronizing HIFU therapy with ultrasound imaging (i.e., as described in the '867 patent) synchronized HIFU signals 82a and ultrasound imaging signals 80a, such that interference 84a due to the HIFU consistently appeared in the same position in each ultrasound image frame.

FIG. 4B schematically illustrates how the technique described herein ensures that HIFU signal 82b and ultrasound imaging signals 80b are offset, such that interference 80b due to the HIFU does not appear in the same position in each ultrasound image frame. The result of the frequency offset is that a band of HIFU-induced interference will sweep across the ultrasound image at a rate corresponding to the difference between the frequency of the ultrasound waves and the frequency of the HIFU waves. This offset can be achieved in a number of different ways. In one embodiment, both the ultrasound imaging system and the therapeutic ultrasound transducer are triggered from a common external trigger (the common external trigger preferably being implemented using a function generator and a set of pulse generators). The external trigger can be controlled such that the interference from the therapeutic ultrasound transducer sweeps across the ultrasound imaging frames, generally as indicated in FIG. 1B above. In another embodiment, the ultrasound imaging system is triggered independently, and the frequency of the square wave used to induce a HIFU duty cycle is varied until the interference from the HIFU sweeps across the ultrasound imaging frames, generally as indicated in FIG. 1B above.

It should be noted that the present technique will reduce the frame rate of the ultrasound images that are ultimately displayed to user. This reduction in frame rate occurs because a plurality of frames, which might ordinarily be immediately displayed to a user, are combined to achieve a single interference-free composite frame. For example, if three frames with interference must be combined to produce an interference-free composite frame, the effective frame rate will be about ⅓ of the actual rate at which frames are generated. This approach thus inherently will reduce the frame rate of the composite images displayed to a user. Significantly, empirical studies have shown that composite interference-free B-mode ultrasound images of HIFU therapy can be obtained using commercial imaging systems, with a HIFU therapy system energized using an 83% duty cycle, by combining 5 image frames to remove the HIFU interference in the entire field of view, with an overall frame rate of 11 frames per second. A frame rate of 11 frames per second, particularly where those frames are interference-free, is quite acceptable. In the empirical study, the therapy system included a 3.23-MHz HIFU transducer (Sonic Concepts, Woodinville, Wash.), driven by a linear amplifier through an electrical matching circuit. The imaging system was an EUB 6000 ultrasound scanner (Hitachi Medical Systems America, Twinsburg, Ohio), with a 7.5-MHz linear transducer. The imaging and therapy systems were synchronized with an external trigger generated using a function generator and a set of pulse generators. B-mode images were acquired sequentially from the EUB 6000 and were then processed offline using the software program MATLAB (The Mathworks Inc., Natick, Mass.). While the images were processed off-line in this study, the results indicate that processing performed in real-time would support the 11 frames per second frame rate noted above.

In the above noted study, sequential ultrasound images were acquired at a frame rate of 54 frames per second, with the scanning window being swept across the imaging frame (i.e., as shown in FIG. 4B). A composite image, substantially similar to that shown in FIG. 3B, was created by combining 5 overlapping imaging frames. The HIFU interference in the composite image was negligible, and the full extent of the hyperechoic spot at the HIFU focus was clearly visible in the composite image. Based on the initial imaging frame rate of 54 frames per second, and that the combining of 5 frames to achieve an interference-free composite image, the overall frame rate is reduced to 11 frames per second.

As discussed above, one advantage of the present technique is that the duty cycle of the HIFU therapy can be increased over that which can be obtained using the synchronization techniques disclosed in the '867 patent. The empirical study noted above also examined the potential benefits of increased duty cycles. On average, when the duty cycle was increased from 50% to 95%, the length of lesions produced by the HIFU increased by 79%, lesion width increased by 47%, and lesion volume increased by 342%. Clearly, increased duty cycles are beneficial. This study further provided empirical evidence that lesion volume can be increased by 160% when the HIFU duration it is increased from 3 to 7 seconds with a 90% duty cycle. Thus, the techniques described herein enable faster real-time image guided HIFU therapy to be achieved, as compared to previous real-time image guided HIFU therapy techniques.

The empirical study further indicates that representative lesion shapes differ for different HIFU duty cycles. HIFU lesions were usually "tadpole shaped" for relatively lower duty cycles and were more irregular in shape for relatively higher duty cycles. Such differences can be attributed to a higher likelihood of cavitational effects at higher duty cycles. Visible "pits" indicative of cavitation-based mechanical tissue damage were observed near the center of the lesion generated using a 90% duty cycle.

Significantly, the empirical study indicates that higher duty cycles introduce more interference into the ultrasound images, and therefore require more raw ultrasound images to be combined to achieve a single interference-free composite image. Logically, the overall frame rate of the composite image decreases proportionally to an increase in the number of overlaps used to create the composite image. For example, using 10 overlaps for a 91% duty cycle causes a 10-fold reduction in the effective frame rate. The composite image frame rate can be increased by restricting the sliding windows to a region of interest (ROI) in the entire frame, as shown in FIG. 4C. A plurality of ultrasound image frames 86 are collected such that imaging is restricted to a narrow ROI 88; the interference-free portions 90 are thus restricted to the narrow ROI of each frame. Using this technique, a duty cycle of 91% can be achieved with five overlaps and a 50% ROI with only a five-fold reduction in the flame rate.

FIG. 5A is a block diagram illustrating a system 92 for generating a composite interference-free ultrasound image from a plurality of ultrasound images that include both interference and interference-free portions. System 92 includes a HIFU transducer 94, a HIFU driving system 104, an ultrasound imaging probe 98, an ultrasound imaging system 100, a processor 102, a display 106, a target 96, and an optional external trigger 108. HIFU transducer 94 and HIFU driving system 104 are conventional, as generally known in the art, and need not be described in further detail. Significantly, ultrasound imaging probe 98 and ultrasound imaging system 100 require no modification, and can be implemented using conventional, commercially available equipment. Target 96 will generally be biological tissue (most often at a site in a human patient), although it should be recognized that the techniques described herein can be employed to enable a composite interference-free ultrasound image to be generated from any target that could be imaged using conventional ultrasound imaging. Display 106 can be implemented using a conventional display and need not be described in greater detail. Processor 102 is preferably implemented using a computing device, such as a personal computer. It should be recognized that it would be possible to implement processor 102 using a customized processor, or an application-specific integrated circuit (ASIC). However, implementing processor 102 using a general processor computing machine instructions for carrying out the steps of FIG. 3A (e.g., software that runs on a conventional personal computer) represents a particularly useful embodiment. Details of a preferred computing device are provided below.

As noted above, in one embodiment, both the ultrasound imaging system and the therapeutic ultrasound transducer are triggered using external trigger 108 (the external trigger preferably being implemented using a function generator and a set of pulse generators). The external trigger can be controlled such that the interference from the therapeutic ultrasound transducer sweeps across the ultrasound imaging frames, generally as indicated in FIG. 1B and FIG. 4B above. In another embodiment, the ultrasound imaging system is triggered independently, and the frequency of the square wave used to induce a HIFU duty cycle is varied until the interference from the HIFU sweeps across the ultrasound imaging frames, generally as indicated in FIG. 1B and FIG. 4B, as discussed above.

FIG. 5B schematically illustrates an exemplary computing system 150 suitable for use in implementing the method of FIG. 3A (i.e., for executing the steps of this method). Exemplary computing system 150 includes a processing unit 154 that is functionally coupled to an input device 152 and to an output device 162, e.g., a display (which can be display 106, but may be any display for the computing system). Processing unit 154 comprises a central processing unit (CPU 158) that executes machine instructions for carrying out a signal processing program that processes a plurality of ultrasound images to combine interference-free portions of those images, generating a composite interference-free ultrasound image. The machine instructions implement functions generally consistent with those described above with respect to FIG. 3A, as well as those described below, with respect to FIG. 6. CPUs suitable for this purpose are available, for example, from Intel Corporation, AMD Corporation, Motorola Corporation, and other sources, as will be well known to those of ordinary skill in this art.

Also included in processing unit 154 are a random access memory (RAM) 156 and non-volatile memory 160, which can include read only memory (ROM) and may include some form of memory storage, such as a hard drive, optical drive, etc. These memory devices are bi-directionally coupled to CPU 158. Such storage devices are well known in the art. Machine instructions and data are temporarily loaded into RAM 156 from non-volatile memory 160. Also stored in the memory are an operating system software and ancillary software. While not separately shown, it will be understood that a generally conventional power supply will be included to provide electrical power at a voltage and current level appropriate to energize computing system 150.

Input device 152 can be any device or mechanism that facilitates user input into the operating environment, including, but not limited to, one or more of a mouse or other pointing device, a keyboard, a microphone, a modem, or other input device. In general, the input device will be used to initially configure computing system 150, to achieve the desired processing (i.e., to process a plurality of ultrasound images to combine interference-free portions of those images to generate a composite interference-free ultrasound image). While not specifically shown in FIG. 5B, it should be understood that computing system 150 is logically coupled to ultrasound imaging system 100, HIFU driving system 104, display 106, and external trigger 108 (when implemented). Configuration of computing system 150 to achieve the desired processing includes the steps of loading appropriate processing software into non-volatile memory 160, and launching the processing application (i.e., loading the processing software into RAM 156) so that the processing application is ready for use. Output device 162 generally includes any device that produces output information, but will most typically comprise a monitor or computer display designed for human perception of output. Use of a conventional computer keyboard for input device 152 and a computer display for output device 162 should be considered as exemplary, rather than as limiting on the scope of this present disclosure.

FIG. 6 is a more detailed flowchart 110 of the technique of FIG. 3A for generating a composite interference-free ultrasound image when non-imaging ultrasound waves (such as HIFU) are present. In a step 112, the HIFU cycle is adjusted such that it is offset from the imaging cycle, generally as described above with respect to FIG. 4B. In a step 114, an ultrasound imaging system is used to obtain a plurality of ultrasound image frames during HIFU therapy. In a step 116, the signals used to produce raw ultrasound images including both interference-free portions and interference are input to a processor for processing. In a working prototype, the ultrasound images are acquired using, for example, the Video for Windows feature in VideoOCX™ video capture software (Marvelsoft of Berlin, Germany). VideoOCX™ provides ActiveX controls that enable a user to grab frames from an incoming video feed. Those of ordinary skill in the art will recognize that many different image processing software applications can be employed to capture a video feed, and the use of VideoOCX™ is intended to be exemplary, rather than limiting.

In a working prototype, the captured video frames were copied to a clipboard using Labview™ (National Instruments Corp., Austin, Tex.) commands, one frame at a time. If HIFU is not being applied, then the image is pasted from the clipboard and any shapes that need to be drawn on the image (such as ovals indicating projected lesion locations) are added to produce a modified image, and the modified image is displayed on the screen of the monitor or display. When the HIFU transducer is turned on, however, large bands of interference appear in the ultrasound image. In order to visualize the target location and apply treatment at the same time, a duty cycle is applied to the HIFU signal, which produces a window on the ultrasound image that is free of interference. A square wave is used to induce the HIFU duty cycle. If the frequency of the square wave is equal to the rate at which the ultrasound probe's elements are interrogated, then the interference window remains stationary (see FIG. 4B). As discussed above, in the present technique the frequency of the square wave can be purposely offset relative to the ultrasound imaging frequency, so that the window sweeps across the ultrasound image. From each frame of video captured, the processor acquires the portion that is free of interference. Once the processor has acquired enough portions that are free of interference to produce a complete image frame, it combines them into one interference-free ultrasound image.

Referring once again to FIG. 6, the processing of the captured ultrasound images will now be described. In a step 118, each raw ultrasound image (i.e., each frame) is split into slices, generally as indicated in FIG. 7. Significantly, interference bands tend to originate at the bottom of ultrasound images and fade as they progress upwards. In a decision step 120, each slice is analyzed to determine if the slice includes interference, or if the slice is interference-free. The process determines if a slice is free of interference by examining a predefined region of pixels that covers roughly the bottom tenth of the slice. A mask is applied to the image that turns all of the pixels but those within the region of interest black. The progression of input image to slice, and then to the predefined region, is shown in FIG. 7, with the masks appearing white in the Figure to make the Figures easier to reproduce.

Statistical values are calculated for the pixel intensities within the predefined region. The values are then used to determine if the slice contains interference bands. Significantly, pixels corresponding to interference can be readily differentiated from pixels corresponding to an interference-free portion of an ultrasound image. Pixels corresponding to interference are characterized by having relatively high pixel intensities, which are relatively consistent across the predefined region. In contrast, pixels corresponding to an interference-free portion of an ultrasound image will generally have lower intensifies, and will exhibit more variability across the predefined region.

If this process determines that a slice is interference-free, the slice is stored temporarily as indicated in a step 122. Once a slice has been stored, no other slices representing the same portion will be stored. In one embodiment, the ultrasound imaging system stops interrogating the region corresponding to a stored slice until an entire interference-free image is obtained, as indicated in a step 124, and the algorithm starts over, to generate the next composite interference-free ultrasound image. This approach prevents the same slice from being incorporated into the composite altar sound image multiple times, which would produce inaccurately bright pixels.

In a decision step 126, the process determines if additional slices are required to generate the interference-free composite image. If so, another slice is selected, and the logic loops back to decision step 120 to process the next slice. If in decision step 120, it is determined that a slice is not interference-free, the logic loops to decision step 126, to determine if additional slices are required to complete the composite image. Once the interference-free composite image is complete, it is displayed as indicated in a step 128. Once the composite image is complete, an additional step can be executed to determine if any overlay shapes need to be incorporated into the composite image. Some overlap may be noted between the slices used to create the composite image. Overlapping portions are discarded during image composition for the single composite image frame.

As noted above, FIG. 7 schematically illustrates how the slicing step of the FIG. 6 can be implemented. A raw ultrasound image frame 130 is selected and broken up into a plurality of slices, as indicated by an exemplary slice 132. Pixel intensities from a small portion 134 of the slice are examined to determine if the slice is interference-free.

FIG. 8 is an image of an exemplary LabView-based user interface 136 that can be used to implement the method of FIG. 3A (particularly in connection with the use of a phased array transducer), and FIGS. 9A-9C are enlarged images of selected portions of exemplary user interface 136. Major functional elements are labeled with white text. Focal depth assignment tools are used to define multiple foci, which are displayed as ovals on the ultrasound-imaging monitor, in the center of the interface. The HIFU duty cycle controls are used to adjust the HIFU interference patterns that appear on the ultrasound image. Treatment parameters are used to define the applied electrical power and total treatment time. Software controlling the interface was written to enable a user to define a number of different focal depths along the transducer axis, either by clicking directly on the ultrasound image in the interface, or by entering a numeric value.

Referring to FIG. 9A, a HIFU properties portion 138 of interface 136 enables the user to define a total power output and duration for the HIFU treatment. The power setting is programmed directly into ultrasound driving system 104 of FIG. 5A, which is in turn, connected to HIFU transducer 94 of FIG. 5A. The value entered for "Time" is used to determine when to disable the driving system after it has been enabled by a "GO!" button. A "Dosage" meter may also be set by the user to automatically determine the power and time settings necessary to produce a desired dosage. Large (and preferably red) "Stop Treatment" and "Abort All" buttons are included in case an error occurs with the hardware, or something goes awry and the HIFU beam and lesions are being generated outside of the desired treatment locations.

FIG. 9B shows a portion 140 of interface 136, which enables a user to set a duty cycle of the HIFU beam, using the slide control labeled "Interference Pattern." A "Left" button and a "Right" button are included in case the user opts to employ a function generator to produce a stationary interference window. By manipulating the "Left" or "Right" button, the user is able to move the ultrasound window to reveal specific regions of the ultrasound image. On-screen pixels to real-life millimeter ratios that correspond to each of the available imaging depths are preferably stored and available for reference, as indicated by the drop down control labeled "Imaging Depth."

Referring now to FIG. 9C, a portion 142 of interface 136 enables a user to control focal parameters of the HIFU beam. The user has the option of defining several focal points automatically, or setting each one independently. Clicking on either of the "Point" buttons permits the assignment of one focal point. A "Line" button produces a line of focal points spaced 5 mm apart (such a dimension is intended to be exemplary, and not limiting). If the user selects a "With Mouse" option, the user can click directly upon the ultrasound image to assign the focal points. A "Numerical" option permits the user to enter specific numerical values, either for the location of a specific focal point or for the ends of a line of focal depths. Regardless of the method that the user selects, the interface will not accept any values outside a range of from about 30 mm to about 60 mm, to ensure that all focal points are within the focusing range of the HIFU transducer (again, such dimensions are intended to be exemplary, and can vary from one transducer to the next). After the user defines the desired focal points, processor 102 determines the phase delays required to drive the HIFU transducer (i.e., when using a phased array transducer in an exemplary implementation) to achieve treatment of the user-defined focal points. An "Auto Step" control, when selected, divides a total treatment time designated by the user into a plurality of equal durations (or steps) for treatment of each defined focal point. If the "Auto Step" control is not selected, the user can manually progress through each focal point, controlling treatment time for each individually, and terminating the process when all desired sites have been treated.

FIG. 10A schematically illustrates a HIFU therapy probe 240 including a phased array transducer that can be controlled using user interface 136 of FIG. 8. HIFU therapy probe 240 includes a generally spoon shaped transducer 242 and a handle 244. Transducer 242 is a phased array transducer including 11 different transducer elements, six of which have complete annuli, and five of which have truncated annuli. Transducer 242 exhibits a focal range of about 3-6 cm.

FIG. 10B illustrates additional details of transducer 242, clearly showing the plurality of different emitter elements that are included therein. Generally spoon-shaped transducer 242 includes 11 discrete emitter elements, all equal in area, each element being separated from its neighbors by about 0.3 mm. Six of the emitter elements have complete annuli, and five emitter elements have truncated annuli. The overall transducer dimensions are about 35 mm×60 mm. Generally spoon-shaped transducer 242 has a center frequency of around 3 MHz, a focal length of about 3-6 cm, a geometric focus of about 5 cm, and a maximum focal intensity of about 3000 W/cm$^2$.

An empirical device implemented transducer 242 with a 3-MHz, 11-element 1-3 composite annular array (Imasonic, Besancon, France), with a matching layer formed from epoxy resin. The natural focus of the array was at 50 mm. Eleven elements were chosen due to economic, ergonomic, and driving hardware constraints. The transducer is elliptically shaped with a length of 60 mm, a width of 35 mm, and a depth of 75 mm, to facilitate transvaginal placement. In an empirical study, the HIFU transducer was connected in series with a custom-built matching network (to match the impedance to 50Ω) and a multi-channel ultrasound driving system (Advanced Surgical Systems, Inc, Tuscon, Ariz.). Eleven amplifier channels were used to drive the array. The driving system was controlled using software written in the LabView programming environment (see user interface 136 of FIG. 8). To display the ultrasound image on the computer screen (FIGS. 8 and 9C), a video capture device (Dazzle 80, Pinnacle Systems, Mountain View, Calif.) was used to capture the video signal from the ultrasound imaging unit. The video data was then imported into the LabView program using ActiveX controls (VideoOCX, Marvelsoft, Berlin, Germany, generally as described above). Processing, generally as described above, is used to generate a composite interference-free image.

The computer communicates with the driving system via an RS-232 connection. The user interface of FIG. 8 is designed to enable the user to individually define an unlimited number of focal depths along the transducer axis, either by clicking directly on the ultrasound image or by typing in the numerical value (see FIG. 9C). In addition, a row of lesions spaced 5 mm apart could be set by designating the start and end of the line within the 30 to 60 mm range. Based on the assumption of constant speed of sound throughout the acoustic path (1500 m/s), the computer (i.e., processor 102, FIG. 5A) calculates the necessary phase delays for each focus. The values are then automatically programmed into the ultrasound driving system using serial commands provided by the manufacturer. In addition to the phase and power settings of each channel, RS-232 serial port commands were used to initiate and terminate ultrasound emission, as well as to enable a shift between focal depths. The total incident electrical power sent to the array was constrained to a range of 0 to 165 W, the latter of which was determined by the manufacturer to be the highest acceptable value for the transducer.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for producing a composite interference-free ultrasound image when non-imaging ultrasound waves would otherwise interfere with ultrasound imaging, comprising the steps of:
   (a) providing a plurality of ultrasound image frames that were produced in the presence of non-imaging ultrasound waves;
   (b) automatically analyzing the plurality of ultrasound image frames to identify interference-free portions of the ultrasound image frames wherein the step of automatically analyzing the plurality of ultrasound image frames to identify interference-free portions comprises the steps of:
      (i) separating an ultrasound image frame into a plurality of slices;
      (ii) for each slice, selecting a predefined portion of the slice;
      (iii) calculating statistical values for pixel intensities in the predefined portion; and
      (iv) based on the statistical values, determining if the predefined portion corresponds to interference, such that if the predefined portion does not correspond to interference the slice is temporarily stored, and if the predefined portion does correspond to interference, discarding the slice; and
   (c) automatically combining a plurality of interference-free portions to generate the composite interference-free ultrasound image.

2. The method of claim 1, further comprising the step of displaying the composite interference-free ultrasound image.

3. The method of claim 1, wherein the step of providing the plurality of ultrasound image frames that were produced in the presence of non-imaging ultrasound waves comprises the step of providing a plurality of ultrasound image frames produced during HIFU therapy.

4. The method of claim 3, wherein the step of providing a plurality of ultrasound image frames produced during HIFU therapy comprises the step of ensuring that a frequency of the HIFU therapy is offset from a frequency of imaging waves used to produce the plurality of ultrasound image frames, so that interference due to the HIFU therapy does not appear in the same place in each of the plurality of frames.

5. The method of claim 4, wherein a difference between the frequency of the HIFU therapy and the frequency of imaging waves used to generate the plurality of ultrasound image frames is sufficiently great to enable a frame rate of the composite interference-free ultrasound image to support a relatively stable display.

6. The method of claim 5, wherein the frame rate of the composite interference-free ultrasound image is greater than about eight frames per second.

7. The method of claim 3, further comprising the step of offsetting the frequency of a square wave used to control the HIFU therapy relative to a frequency of imaging waves used to generate the plurality of ultrasound image frames, so that interference due to the HIFU therapy does not appear in the same place in each of the plurality of ultrasound image frames.

8. The method of claim 1, further comprising the step of directing a signal corresponding to each of the plurality of ultrasound image frames to a computing device for processing to generate the composite interference-free ultrasound image.

9. The method of claim 1, wherein the step of combining the plurality of interference-free portions to generate a composite frame comprises the step of combining stored slices until the interference-free ultrasound image is achieved.

10. The method of claim 1, further comprising the step of discarding additional slices corresponding to a stored slice, to prevent the composite interference-free ultrasound image from including inaccurately bright pixels.

11. The method of claim 1, wherein the step of selecting the predefined portion from the slice comprises the step of selecting a bottom portion of the slice.

12. The method of claim 1, further comprising the step of determining if an overlay is to be incorporated into the composite interference-free ultrasound image, and if so, incorporating the overlay into the composite interference-free ultrasound image.

13. The method of claim 1, further comprising the step of restricting a scanning window associated with an ultrasound imaging system used to produce the plurality of ultrasound image frames to a defined limited portion of an ultrasound image frame, to increase a frame rate at which the composite interference-free ultrasound image is generated.

14. A memory medium on which are stored machine instructions employed for carrying out a plurality of steps, wherein the plurality of steps include:
  (a) capturing a plurality of ultrasound image frames acquired in the presence of non-imaging ultrasound waves;
  (b) automatically analyzing the ultrasound image frames to identify interference-free portions of the ultrasound image frames by:
    (i) separating an ultrasound image frame into a plurality of slices;
    (ii) for each slice, selecting a predefined portion of the slice;
    (iii) calculating statistical values for pixel intensities in the predefined portion; and
    (iv) based on the statistical values, determining if the predefined portion corresponds to interference, such that if the predefined portion does not correspond to interference, the slice is temporarily stored, and if the predefined portion does correspond to interference, discarding the slice; and
  (c) automatically combining a plurality of interference-free portions to generate a composite interference-free ultrasound image.

15. The memory media of claim 14, wherein the machine instructions are further employed for carrying out the step of displaying the composite interference-free ultrasound image.

16. The memory media of claim 14, wherein the machine instructions are further employed for carrying out the step of enabling a user to select a frequency of the non-imaging ultrasound waves, such that the selected frequency is different than a frequency of ultrasound imaging waves used to acquire the plurality of ultrasound image frames, thereby ensuring that interference in the plurality of ultrasound image frames due to the non-imaging ultrasound waves does not appear in the same position in each ultrasound image frame.

17. The memory media of claim 14, wherein the machine instructions are further employed for carrying out the step of combining stored slices until the interference-free ultrasound image is achieved.

18. The memory media of claim 14, wherein the machine instructions are further employed for carrying out the step of discarding additional slices corresponding to a stored slice, to prevent the composite interference-free ultrasound image from including inaccurately bright pixels.

19. The memory media of claim 14, wherein the machine instructions are further employed for carrying out the step of selecting the predefined portion from a bottom of the slice.

20. A system for obtaining a composite interference-free ultrasound image when non-imaging ultrasound waves would otherwise interfere with ultrasound imaging, comprising:
  (a) an ultrasound imaging system configured to generate a plurality of ultrasound image frames; and
  (b) a processor logically coupled to the ultrasound imaging system and configured to implement a plurality of functions, including:
    (i) capturing a plurality of ultrasound image frames acquired in the presence of non-imaging ultrasound waves;
    (ii) automatically analyzing the ultrasound image frames to identify interference-free portions of the ultrasound image frames by:
      (A) separating an ultrasound image frame into a plurality of slices;
      (B) for each slice, selecting a predefined portion of the slice;
      (C) calculating statistical values for pixel intensities in the predefined portion; and
      (D) based on the statistical values, determining if the predefined portion corresponds to interference, such that if the predefined portion does not correspond to interference, the slice is temporarily stored, and if the predefined portion does correspond to interference, discarding the slice; and
    (iii) automatically combining the interference-free portions to generate a composite interference-free ultrasound image.

* * * * *